United States Patent [19]
Curtis et al.

[11] Patent Number: 5,464,427
[45] Date of Patent: Nov. 7, 1995

[54] EXPANDING SUTURE ANCHOR

[75] Inventors: Raymond L. Curtis, Davos Dorf; Urs Schlegel, Davos-Platz; Thomas Heldstab, Davos Dorf, all of Switzerland

[73] Assignee: Synthes (U.S.A.), Paoli, Pa.

[21] Appl. No.: 317,396

[22] Filed: Oct. 4, 1994

[51] Int. Cl.$^6$ .................................................. A61B 17/00
[52] U.S. Cl. ............................... 606/232; 606/72; 411/60
[58] Field of Search ..................................... 606/232, 116, 606/148, 60, 63, 65, 66, 68, 72, 73, 75; 24/453; 411/60, 54, 41, 45–48

[56] References Cited

U.S. PATENT DOCUMENTS

| | | | |
|---|---|---|---|
| 4,738,255 | 4/1988 | Goble et al. | 606/232 |
| 5,258,016 | 11/1993 | DiPoto et al. | 606/232 |
| 5,336,240 | 8/1994 | Metzler et al. | 606/72 |
| 5,354,298 | 10/1994 | Lee et al. | 606/72 |

Primary Examiner—Tamara L. Graysay
Assistant Examiner—Jeffrey A. Schmidt
Attorney, Agent, or Firm—Davis Hoxie Faithfull & Hapgood

[57] ABSTRACT

The suture anchor comprises a first main body (11) of a generally cylindrical shape having a front portion (1), a rear portion (2), a longitudinal axis (3), a curved surface (4) with protrusions (5), a central through-going bore (19) extending from said front portion (1) to said rear portion (2), and a longitudinal slit (12) which opens at said front portion (1) and curved surface (4) and is closed at said rear portion (2).

It further comprises a second conical body (14) having a smaller base (15), a larger base (16), a curved surface (17) and a longitudinal axis (13), said second conical body (14) being coaxially introducible with its smaller base (15) into said slit (12) thereby causing expansion of said first main body (11). The second conical body (14) is provided with a through-hole (6) running transversely to said longitudinal axis (13) and two channels (7) positioned on said curved surface (17) and extending from the orifices (18) of said through-hole (6) to said smaller base (15).

15 Claims, 3 Drawing Sheets

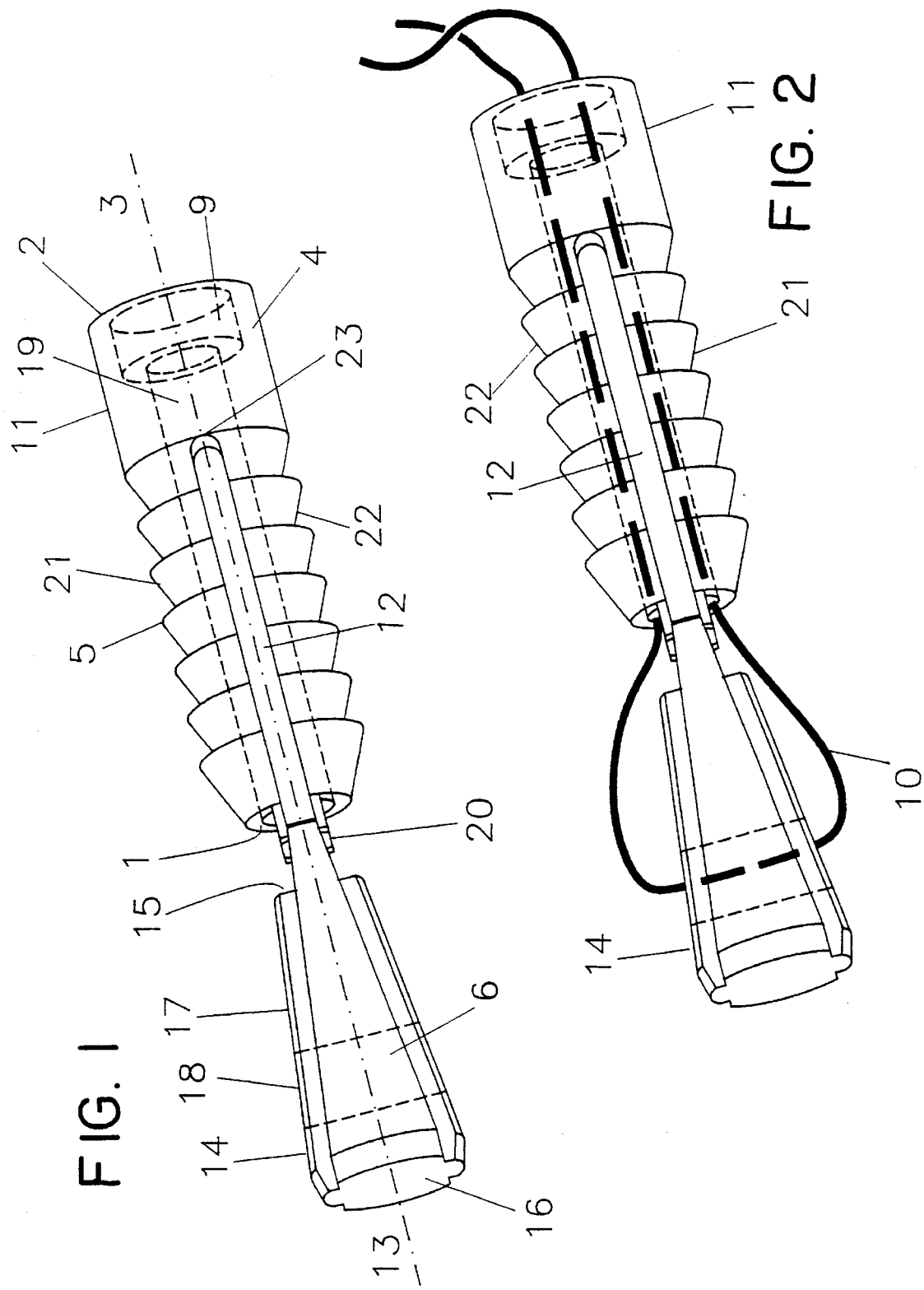

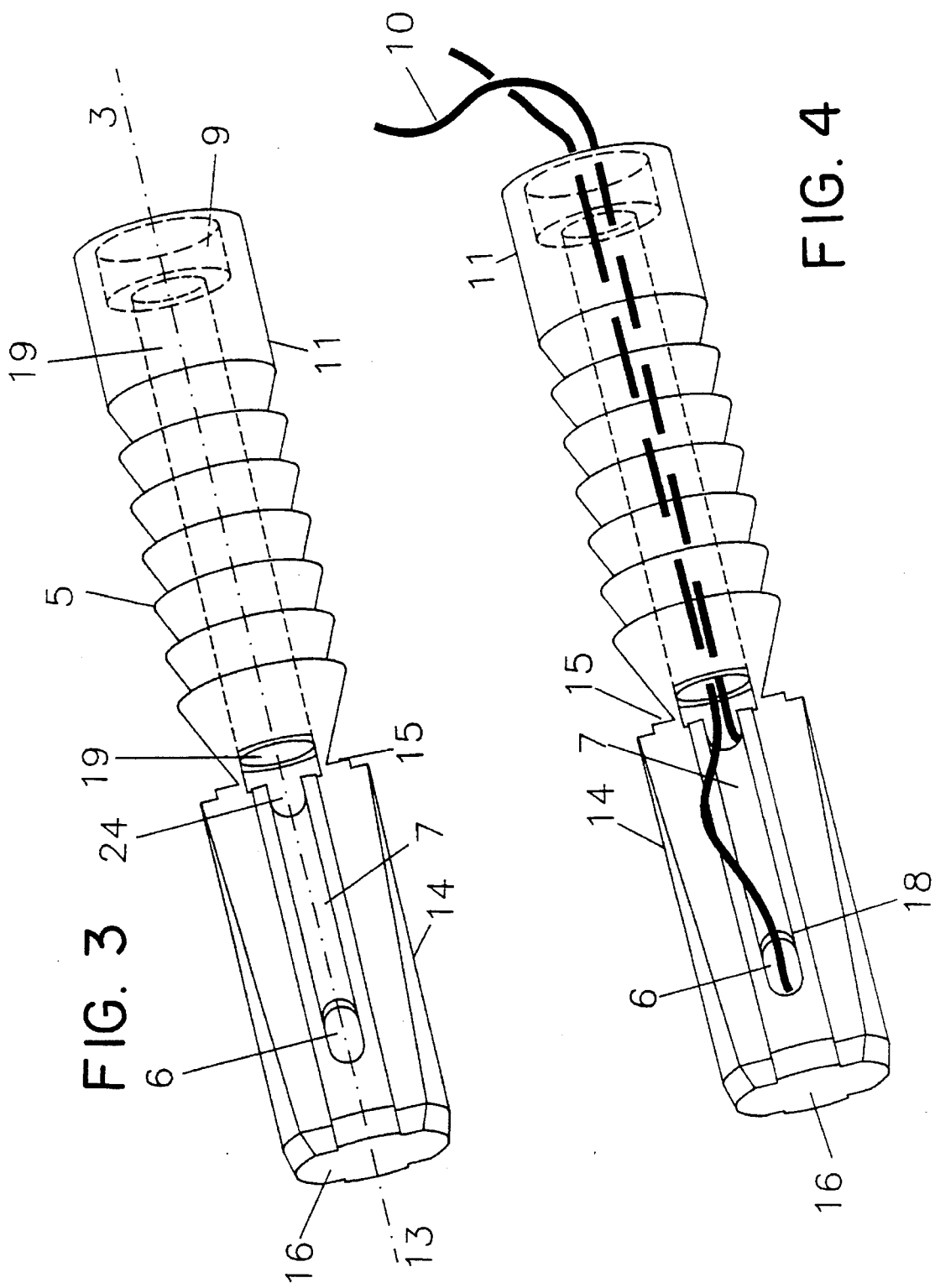

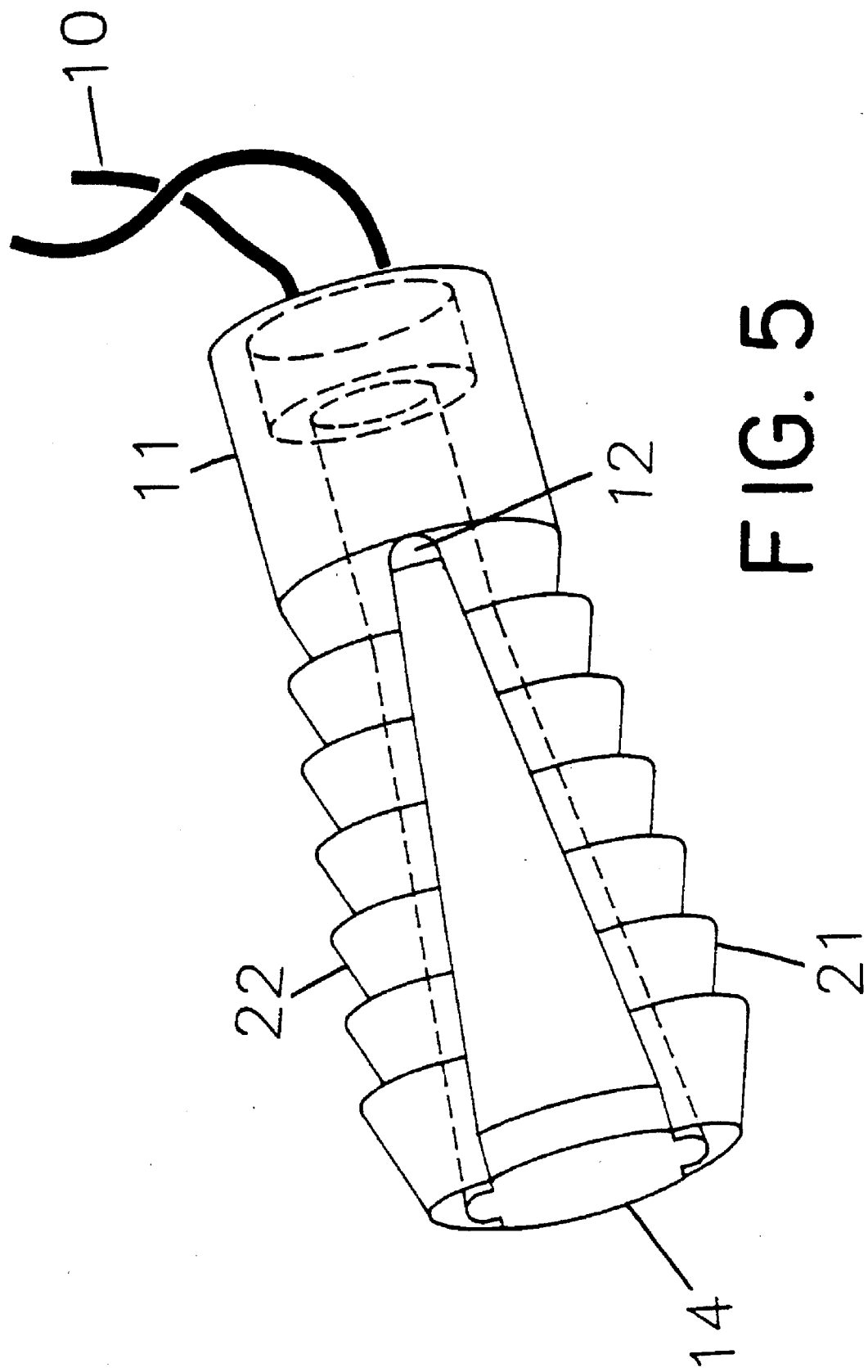

EXPANDING SUTURE ANCHOR

FIELD OF THE INVENTION

This invention relates to a suture anchor.

Sutures are used in surgery i.a. for attachment of soft tissue to bone. They are used in repair of tissue avulsions from bone as well as in reconstructive procedures, including reattaching avulsed tendons, ligaments and joint capsules to bone. The field of application extends to treatment of shoulder instability and rotator cuff tears, knee instability, maxillofacial surgery, hand surgery and ligamentous repair of the foot, ankle and wrist. The shoulder is of particular interest because dislocation of this joint occurs more frequently than any other human joint causing limitation of motion and pain in athletes and nonathletes of all ages.

Anchoring of the suture is either made directly in the bone mass or by means of an anchor to be implanted into the bone.

BACKGROUND ART

The classic BANKART procedure is a widely accepted method of treating anterior-inferior gleno-humeral instability, using sutures that are inserted directly through transosseous tunnels without an anchor. Although the surgical exposure involves minimal trauma and skin incision and leads to excellent clinical results with reported recurrence rates of 3.5% to 4.0%, the procedure of reattaching the torn ligament or tendon can be time consuming and difficult. While modifications that decrease the operating time for standard rotator cuff and Bankart lesion repairs are available, these approaches are technically demanding.

The use of staples has a tendency to cut through the bone and tendon.

An expanding suture anchor is known from EP-A1 0 502 509 having a slotted main body and a second conical body being coaxially introducible therein thereby causing expansion of said main body.

The suture is trapped upon assembly of the expanding suture anchor (between the main body and the conical body), so that the suture is not free to slide upon assembly. The entrapping of the suture causes furthermore a reduction in the ultimate tensile strength of the suture.

SUMMARY OF THE INVENTION

The invention as claimed aims at solving the above described problems by providing a suture anchor which can be easily and safely assembled without blocking of the suture in the anchor. The sliding quality of the suture after assembly of the expanding suture anchor is very important for the surgeon in order to apply a sliding knot to the suture.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

BRIEF DESCRIPTION OF THE DRAWINGS

In the drawings:

FIG. 1 is a perspective view of the expanding suture anchor according to the invention prior to introduction of the suture;

FIG. 2 is a perspective view of the expanding suture anchor according to the invention after introduction of the suture;

FIG. 3 is a perspective view of the expanding suture anchor according to FIG. 1 rotated by 90°;

FIG. 4 is a perspective view of the expanding suture anchor according to FIG. 2 rotated by 90°; and FIG. 5 is a perspective view of the expanding suture anchor after introduction of the conical part into the main body and expansion of the latter.

DETAILED DESCRIPTION OF THE INVENTION

The suture anchor as represented in FIGS. 1 to 4 consists basically of a first main body 11 and a conical body 14.

The main body 11 has a generally cylindrical shape with a front portion 1, a rear portion 2 and a longitudinal axis 3. The curved surface 4 of the main body 11 is provided with protrusions 5, in the form of barbs distributed over the full length of the main body to facilitate retention of the suture anchor in cortical bone or cortical and cancellous bone. The rear portion 2 is provided with connection means 9 in the form of a central hole for receiving a manipulation instrument. A central through-going bore 19 extends from the front portion 1 to the rear portion 2 for receiving the two ends of the loop of suture 10.

A longitudinal slot 12 which opens at the front portion 1 and curved surface 4 and is closed at the rear portion 2 allows for the expansion of the main body 11. The closed end 23 of slot 12 is rounded in order to evenly distribute stresses when the two legs 21,22 are spreaded.

The second conical body 14 has a smaller base 15, a larger base 16, a curved surface 17 and a longitudinal axis 13. This second conical body 14 is coaxially introducible with its smaller base 15 into the slot 12 of the first main body 11 thereby causing expansion of the latter. The expansion of the suture anchor leads to an improved fixation of the anchor in the bone mass. A through-hole 6 is running transversely to the longitudinal axis 13' of the conical body 14 and is destined to receive the suture 10. The through-hole 6 is located at a distance from the larger base 15 which corresponds to 5 to 25 % of the total length of the conical body 14. This location results in maximum strength of the suture fixation.

Two channels 7 are positioned on the curved surface 17 of the conical body 14 and extend from the orifices 18 of the through-hole 6 to the smaller base 15. The function of the channels 7 is to take up the suture 10—as shown in FIGS. 3 and 4—after its introduction in the through-hole 6 and to prevent its blocking between the curved surface 17 and the main body 11 (the suture 10 is passed through the through-hole 6 prior to assembly of the anchor). To this effect the depth of these channels 7 should exceed the smallest diameter of the through-hole 6. The depths of the channels 7 may diminish from said orifices 18 to said smaller base 16 due to the conical shape of the conical body 14.

The course of the through-hole 6 is either straight, rendering easy its manufacture, or preferably curved whereby its apex is facing the larger base 16. The curved configuration allows a smooth running of the suture 10 within the through-hole 6 and prevents sharp edges which could lead to damage of the suture 10.

The main body 11 and the conical body 14 may either be two distinct parts or—as shown in FIGS. 1 to 4—temporarily connected coaxially by an intermediate portion 20, which upon applying a certain pulling force to the suture 10 breaks away bringing the conical body 14 in abutment with the main body 11 as shown in FIGS. 3 and 4. The application of the pulling force occurs by holding the main body 11 with a suitable instrument using the connecting means 9 and pulling the two ends of the loop of suture 10 introduced through the trough hole 6 and the central bore 19. The intermediate portion 20 is provided with a passage 24 for allowing space for introduction of the suture 10 between the main body 11 and the conical body 14.

As shown in FIG. 5, upon further pulling of the suture 10 the conical body 14 enters slot 12 with its smaller base 15 and spreads the two legs 21,22 formed by said slot 12 leading to expansion of said main body 11 and fixation thereof in the bone mass.

The suture anchor can be made of any known implant material, e.g. stainless steel or titanium. Preferably it is made of a resorbable material, e.g. a polylactide. In the presence of enzymes in the human body, polylactides degrade to lactic acid, and subsequently to carbon dioxide and water. These are removed from the body via respiratory routes and kidneys respectively. By using resorbable materials irritation of soft tissue from metallic corrosion is eliminated. It also eliminates interference with certain imaging diagnostic or therapeutic treatments near the site, such as magnetic resonance imaging, and where the use of such imaging is indicated any metal implants may first have to be surgically removed.

Preferably the suture anchor has an over-all length of 21 mm at most (preferably 18 mm at most) before introduction into the bone. In a restricted area such as the shoulder, this limited dimension (compared to prior art devices which are 25 mm long) gives the clinician more freedom of choice for the site of insertion.

While the foregoing description and drawings represent the preferred embodiments of the present invention, it will be obvious for those skilled in the art that various changes and modifications may be made therein without departing from the true spirit and scope of the present invention.

We claim:

1. Suture anchor comprising

A) a first main body (11) of a generally cylindrical shape having a front portion (1) for facing a body member to be treated, a rear portion (2), a longitudinal axis (3), a curved surface (4), a central through-going bore (19) extending from said front portion (1) to said rear portion (2), and a longitudinal slit (12) which opens at said front portion (1) and at said curved surface (4) and is closed at said rear portion (2);

B) a second conical body (14) having a smaller base (15), a larger base (16), a curved surface (17) and a longitudinal axis (13), said second conical body (14) being coaxially introducible with its smaller base (15) into said slit (12) thereby causing expansion of said first main body (11), said second conical body (14) being provided with a through-hole (6) running transversely to said longitudinal axis (13); and C) two channels (7) positioned on said curved surface (17) of said second conical body (14) and extending from the orifices (18) of said through-hole (6) to said smaller base (15).

2. Suture anchor according to claim 1, characterized in that said through-hole (6) is located at a distance from said larger base (16) which corresponds to 5 to 25% of the total length of said second conical body (14).

3. Suture anchor according to claim 1, wherein said through-hole (6) is longitudinally curved with the apex facing said larger base (16).

4. Suture anchor according to claim 1, wherein said rear portion (2) is provided with connection means (9) for releasably receiving a manipulation instrument.

5. Suture anchor according to claim 1, and made from a resorbable material.

6. Suture anchor according to claim 1, wherein said curved surface (4) is provided with protrusions (5).

7. Suture anchor according to claim 6, wherein said protrusions (5) are threads or barbs.

8. Suture anchor according to claim 1, wherein said main body (11) and said conical body (14) are temporarily connected coaxially by an intermediate portion (20), which upon applying a predetermined axial force breaks away bringing said conical body (14) in abutment with said main body (11).

9. Suture anchor according to claim 1, wherein the closed end (23) of said longitudinal slot (12) is rounded.

10. Suture anchor according to claim 1, having an over-all length of not more than 21 mm before introduction into the bone.

11. Suture anchor according to claim 1, wherein and having an over-all length of not more than 18 mm before introduction into the bone.

12. Suture anchor according to claim 1 and made from a polylactide.

13. Suture anchor comprising

A) a first body 11 of a generally cylindrical shape having a front portion (1), a rear portion (2), a longitudinal axis (3), a curved surface (4), a central through-going bore (19) extending from said front portion (1) to said rear portion (2), and a longitudinal slit (12) which opens at said front portion (1) and at said curved surface (4) and is closed at said rear portion (2);

B) a second conical body (14) having a smaller base (15), a larger base (16), a curved surface (17), and a longitudinal axis (13), said second conical body (14) being coaxially introducible with its smaller base (15) into said slit (12), thereby causing expansion of said first main body (11), said second conical body (14) being provided with a through hole (6) running transversely to said longitudinal axis; and C) two channels (7) positioned on said curved surface (17) of said second conical body (14) extending from the orifices (18) of said through hole (6) to said smaller base (15), said channels (7) having a depth exceeding the smallest diameter of said through hole (6).

14. Suture anchor comprising

A) a first main body (11) of a generally cylindrical shape having a front portion (1), rear portion (2), a longitudinal axis (3), a curved surface (4), a central through-going bore (19) extending from said front portion (1) to said rear portion (2), and a longitudinal slit (12) which opens at said front portion (1) and at said curved surface (4) and is closed at said rear portion (2);

B) a second conical body (14) having a smaller base (15), a larger base (16), a curved surface (17) and a longitudinal axis (13), said second conical body (14) being coaxially introducible with its smaller base (15) into said slit (12) thereby causing expansion of said first body (11), said second conical body (14) being provided with a through hole (6) running transversely to said longitudinal axis (13), and C) two channels (7) positioned on said curved surface

(17) of said second conical body (14) and extending from the orifices (18) of said through hole (6) to said smaller base (15), the depth of said channels (7) diminishing from said orifices (18) to said smaller base (16).

15. Suture anchor comprising

A) a first main body (11) of a generally cylindrical shape having a front portion for facing a body member to be treated (1), a rear portion (2), a longitudinal axis (3), a curved surface (4), a central through-going bore (19) extending from said front portion (1) to said rear portion (2), and a longitudinal slit (12) which opens at said front portion (1) and at said curved surface (4) and is closed at said rear portion (2);

B) a second body (14) having a smaller base (15), a larger base (16), a curved surface (17) and a longitudinal axis (13), said second body (14) being coaxially introducible with its smaller base (15) into said slit (12) thereby causing expansion of said first main body (11), said second body (14) being provided with a through-hole (6) running transversely to said longitudinal axis (13); and C) two channels (7) positioned on said curved surface (17) of said second body (14) and extending from the orifices (18) of said through-hole (6) to said smaller base (15).

* * * * *